(12) United States Patent
Kelso et al.

(10) Patent No.: US 10,843,195 B2
(45) Date of Patent: Nov. 24, 2020

(54) DEVICES, SYSTEMS, AND METHODS FOR SPECIMEN PREPARATION USING CAPILLARY AND CENTRIFUGAL FORCES

(71) Applicant: Northwestern University, Evanston, IL (US)

(72) Inventors: David M. Kelso, Evanston, IL (US); Robert Elghanian, Evanston, IL (US)

(73) Assignee: Northwestern University, Evanston, IL (US)

( * ) Notice: Subject to any disclaimer, the term of this patent is extended or adjusted under 35 U.S.C. 154(b) by 207 days.

(21) Appl. No.: 15/759,074

(22) PCT Filed: Sep. 9, 2016

(86) PCT No.: PCT/US2016/050930
§ 371 (c)(1),
(2) Date: Mar. 9, 2018

(87) PCT Pub. No.: WO2017/044732
PCT Pub. Date: Mar. 16, 2017

(65) Prior Publication Data
US 2019/0046983 A1    Feb. 14, 2019

Related U.S. Application Data
(60) Provisional application No. 62/216,125, filed on Sep. 9, 2015.

(51) Int. Cl.
*B01L 3/00* (2006.01)
*G01N 33/487* (2006.01)

(52) U.S. Cl.
CPC ...... *B01L 3/502753* (2013.01); *G01N 33/487* (2013.01); *B01L 2200/0684* (2013.01); *B01L 2300/069* (2013.01); *B01L 2300/0681* (2013.01); *B01L 2300/0816* (2013.01); *B01L 2300/0874* (2013.01); *B01L 2300/0887* (2013.01); *B01L 2400/0406* (2013.01); *B01L 2400/0409* (2013.01)

(58) Field of Classification Search
CPC ....... B01L 3/502753; B01L 2200/0684; B01L 2300/0681; B01L 2300/069; B01L 2300/0816; B01L 2300/0874; B01L 2300/0887; B01L 2400/0406; B01L 2400/0409; G01N 33/487
See application file for complete search history.

(56) References Cited

U.S. PATENT DOCUMENTS

| | | |
|---|---|---|
| 6,752,961 B2 | 6/2004 | Kopf-Sill et al. |
| 8,377,710 B2 | 2/2013 | Whitesides et al. |
| 8,465,698 B2 | 6/2013 | Yamakawa et al. |

(Continued)

OTHER PUBLICATIONS

International Search Report and Written Opinion for PCT/US2016/050930, dated Nov. 29, 2016, 13 pages.

*Primary Examiner* — William H. Beisner
*Assistant Examiner* — Danielle B Henkel
(74) *Attorney, Agent, or Firm* — Casimir Jones SC; David W. Staple (57) ABSTRACT

Provided herein are devices, systems, and methods for specimen preparation by employing a combination of capillary and centrifugal forces. For example, provided herein are devices, systems, and methods that collect a sample by capillary force, separate components of the collected sample by centrifugal force, and isolate one or more of the separated components by further capillary force.

13 Claims, 10 Drawing Sheets

(56) References Cited

U.S. PATENT DOCUMENTS

| | | |
|---|---|---|
| 2006/0078873 A1 | 4/2006 | Ogawa et al. |
| 2009/0074620 A1 | 3/2009 | Therup et al. |
| 2009/0191643 A1 | 7/2009 | Boehm et al. |
| 2012/0142019 A1 | 6/2012 | Miller |

DEVICES, SYSTEMS, AND METHODS FOR SPECIMEN PREPARATION USING CAPILLARY AND CENTRIFUGAL FORCES

CROSS REFERENCE TO RELATED APPLICATIONS

The present invention claims the priority benefit of U.S. Provisional Patent Application 62/216,125, filed Sep. 9, 2015, which is incorporated by reference in its entirety.

FIELD

Provided herein are devices, systems, and methods for specimen preparation by employing a combination of capillary and centrifugal forces. For example, provided herein are devices, systems, and methods that collect a sample by capillary force, separate components of the collected sample by centrifugal force, and isolate one or more of the separated components by further capillary force.

BACKGROUND

Pre-analytic sample collection and preparation represent important steps in the analysis of biological and environmental samples. Most analytical technologies that detect substances or molecules of interest rely on at least one, if not multiple, sample preparation steps before the analysis can occur. Samples such as blood often must be collected from finger or heal sticks, or be sampled from collection containers such as a VACUTAINER device. For example, the detection of RNA, DNA, or proteins, whether native to a sample or from a foreign source (e.g., infectious disease agent, etc.) from biological samples such as blood, urine, saliva, cerebrospinal fluid, or the like often require that the target molecule of interest be separated from other components of the sample (e.g., cells, nucleases, proteases, inhibitors that are incompatible with the analysis assay, components that create background noise in the analytical technique, etc.). A wide variety of technologies have been developed to facilitate such sample collection and preparation. A common feature of many of these technologies is the need for complex and/or expensive equipment or reagents. While such technologies are acceptable in some applications and settings, they are unduly burdensome in others. For example, the cost and complexity of existing technologies makes them unaffordable, unavailable, or unusable in situations where funds are not available or where highly skilled technicians are not present. What are needed are low cost, easy to use alternatives.

SUMMARY

Provided herein are devices, systems, and methods for specimen preparation by employing a combination of capillary and centrifugal forces. For example, provided herein are devices, systems, and methods that collect a sample by capillary force, separate components of the collected sample by centrifugal force, and isolate one or more of the separated components by further capillary force. The devices, systems, and method allow one to: 1) obtain a precise volume of a sample or sample component (e.g., plasma) regardless of the volume of sample (e.g., blood) collected or its properties (e.g., hematocrit); 2) utilize existing centrifuge devices to generate the centrifugal forces (e.g., fit the discharge end of the device into a small diameter test tube); 3) assure sufficient volume of sample collected (e.g., finger and heel stick collection devices are difficult to use); and 4) eliminate the need to pipet aliquot sample (e.g., plasma) (many medical workers are not skilled at pipetting).

Figure 1:
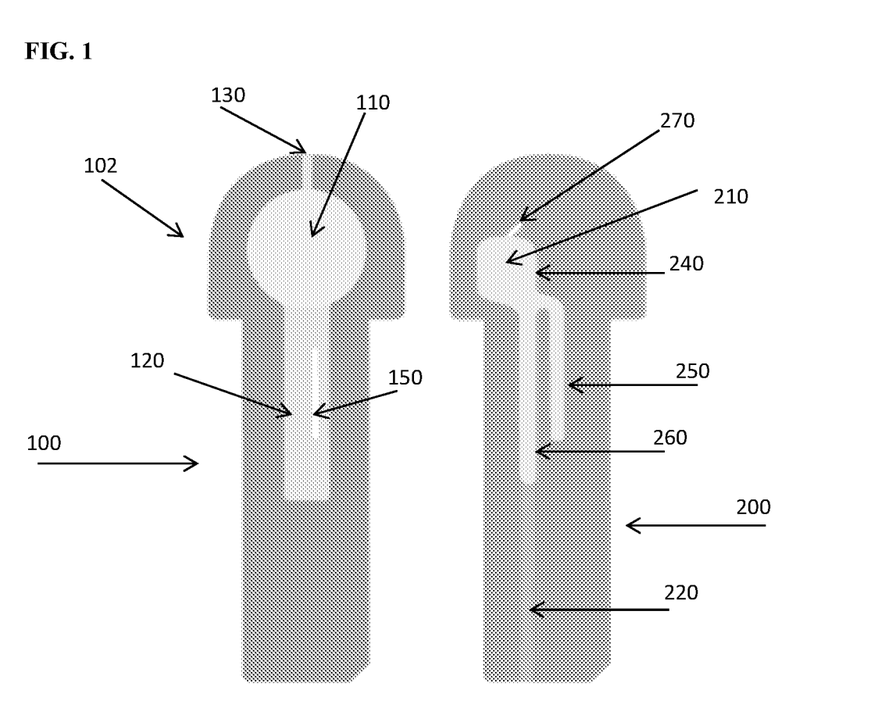
FIG. 1 shows a diagram of two layers of an embodiment of a device. The left panel shows a first layer having a sample collection zone and a reservoir. The right panel shows a second layer having a sample metering zone and discharge channel.

For example, in some embodiments, provided herein is a device (e.g., device 100 of FIG. 1) for sample preparation (e.g., metering of a specific amount of a sample, separation of components of a sample), comprising: a) a sample collection zone comprising a porous membrane (e.g., a sample collection pad 110 of FIG. 1); b) a separation zone (e.g., a separation chamber 120 of FIG. 1) in fluid communication with the sample collection zone and positioned relative to the sample collection zone such that a centrifugal force applied along an axis of the device moves a collected sample from the sample collection zone to the separation zone; and c) a sample metering zone (e.g., a reservoir 240 of FIG. 1) comprising a porous membrane (e.g., a metering pad 210 of FIG. 1), the sample metering zone in passive fluid communication with a portion of the separation zone, but not the sample collection zone (e.g., via capillary force through slit opening 150 of FIG. 1). The portion of the separation zone in fluid communication with the sample metering zone can be selected by placing a hole, slit, or other passage between the two zones at the desired physical location. Where components of a sample are to be separated, if a less dense component is desired to be transferred from the separation zone to the sample metering zone, the passage can be placed near the upper region of the separation zone such that a less dense, isolated component of the sample residing near the top separation zone preferentially migrates into the porous membrane of the sample metering zone via capillary force. A key advantage of the device is that the porous membranes can transport sample in all directions, while the centrifugal force only transports sample radially away from the axis of rotation.

In some embodiments, the device further comprises an air vent (e.g., a first air vent; e.g., air vent 130 of FIG. 1) in fluid communication with the sample collection zone. In some embodiments, the device further comprises an air vent (e.g., a second air vent; e.g., air vent 270 of FIG. 1) in fluid communication with the sample metering zone.

In some embodiments, the device further comprises a discharge channel (e.g., discharge channel 220 of FIG. 1) in fluid communication with the sample metering zone and positioned radially outward from the axis of rotation such that a centrifugal force moves an aliquot of sample from the sample metering zone to the discharge channel, and ultimately, out of the device or into a processing chamber in the device or attachable to the device.

In some embodiments, sample moves from the separation zone to the sample metering zone through a slit opening, hole, or other passageway between the separation zone and the sample metering zone.

The device may be manufactured as a single unit or may comprise two or more layers that are attached to one another via any suitable mechanism (e.g., adhesive, snaps, welds, etc.). In some embodiments, a single unit is molded with the sample collection zone and separation zones one side and the sample metering zone on the other size, separated by a slit. Porous membranes are inserted into the sample collection zone and sample metering zones and the device is sealed with addition of film or other covers. Alternatively, in some embodiments, the device comprises two layers: a first layer comprising the sample collection zone and the separation zone; and a second layer below the first layer, the second layer comprising the sample metering zone. In some embodiments, a third layer is employed, disposed between the first layer and the second layer, the third layer comprising the slit opening. The device may further comprise first and/or second (e.g., front and/or back) covers. For example, in some embodiments, the device comprises a first (e.g., front) cover configured to cover the sample collection zone (e.g., the front cover comprising an opening positioned to allow a sample (e.g., blood from a finger or heel prick), exterior to the device, to contact and enter the sample collection zone via capillary force). In some embodiments, a cover is provided to seal or close the opening after the sample is added. The cover may comprise sticker, tape, sliding door, or any other desired mechanism. The cover finds use, for example, to prevent evaporation of sample from the sample collection zone while the device is in use. In some embodiments, a second cover (e.g., back cover) is configured to cover the sample metering zone, the back cover comprising the second air vent in fluid communication with the sample metering zone.

The size and shape of each of the zones and passages is selected based on, among other factors, the nature of the sample to be processed, the volume of the sample, the volume of a desired isolated component of the sample, the physical properties of the sample, the degree of purification/isolation desired, the amount of centrifugal force employed, and the capillary force of the porous membrane. The selection of material and manufacturing specification may also take these factors into account.

In some embodiments, the sample metering zone comprises two or more sub-regions (e.g., branches). In some such embodiments, the sample metering zone comprises a first branch in fluid communication with the separation zone via the slit opening and a second branch not in direct fluid communication with the slit opening. Such embodiments, find use, for example, to ensure that any contamination of an undesired sample component that migrates into the sample metering zone is isolated in the first sub-region/branch. In some embodiments, the second branch is in fluid communication with the discharge channel.

In some embodiments, the device is a small hand-held device. In assembled form, the device has a length, width, and depth. In some embodiments, these dimensions are selected to permit the device to fit within a collection tube and/or a centrifuge tube or bucket. In some embodiments the length is less than 20 cm (e.g., <15, 12, 10, 9, 8, 7, 6, 5, 4, 3, 2, 1 cm; or values or ranges therein between, e.g., between 5-10 cm; 5.5 cm). In some embodiments, the width is less than 10 cm (e.g., <9, 8, 7, 6, 5, 4, 3, 2, 1, 0.5, 0.25 cm; or values or ranges therein between, e.g., between 1-4 cm; 2.5 cm). In some embodiments, the depth is less than 5 cm (e.g., <5, 4, 3, 2, 1, 0.5, 0.25, 0.1 cm; or values or ranges therein between, e.g., between 0.5-1 cm; 0.7 cm).

In use, the devices may further comprise the sample. A collected sample (e.g., blood sample) may be present in the porous membrane of the sample collection zone. Further, after centrifugation, the sample be a in the separation zone, potentially separated into two or more components. Following centrifugation, the sample or one or more separated components thereof may reside in the porous membrane of the sample metering zone. Following further centrifugation, one or more separated components may be in a collection container (e.g., collection tube).

In some embodiments, porous membranes are coated or integrated with one or more reagents or other components that facilitate sample processing. For example, in some embodiments, the collection membrane comprises an anticoagulant when the sample is blood. In some embodiments, the metering membrane comprises (e.g., is coated with) a stabilizing reagent or assay reagent. Such reagents include but are not limited to buffering salts, bases, acids, enzyme inhibitors, affinity reagents, detectable labels, nucleases, proteases, and the like.

The device may be provided with and used in conjunction with a system. In some embodiments, a kit is provided containing the device and other components. For example, in some embodiments, systems and kits comprise a centrifuge. The centrifuge is any equipment that generates centrifugal force to the separation device—i.e., that puts an object in rotation around a fixed axis. This includes manual and electronic centrifuges. It includes fixed angle, swinging head or bucket, and continuous tubular centrifuges. In some embodiments, the system and/or kit comprises one or more collection tubes, spare porous membranes, sample collection instruments (syringes, etc.), instructions for use, data analysis instruments and/or software, reagents and/or equipment for analyzing the isolated sample component, and the like.

Further provided herein are uses of any of the devices or systems described above or elsewhere herein. Any and all uses are contemplated. In some embodiments, the use is the isolation of a component from a sample (e.g., plasma from blood).

Thus, in some embodiments, provided herein are methods comprising the step of metering a sample or isolating a component of a sample using a device or system described herein. In some embodiments, the method comprises one or more or all of the steps (in any order unless specified otherwise) of: a) contacting the porous membrane in the sample collection zone with the sample such that the sample enters the porous membrane via capillary forces; b) applying centrifugal force (e.g., a first centrifugal force) to the long axis of the device to move at least a portion of the sample from the sample collection zone to the separation zone and, if desired, to separate the sample into a first component and a second component (e.g., using a second centrifugal force which, in some embodiments, is greater than the first centrifugal force is applied for a longer period of time, or both); c) reducing or stopping the centrifugal force such that the sample or first component in the separation zone moves via capillary force into the sample metering zone; d) applying centrifugal force to the long axis of the device to move the sample or first component out of the device through the discharge channel; e) capturing the sample or first component in a process vessel; and f) analyzing the sample or first component.

Also provided herein are methods of metering a sample and/or separating components from a sample, comprising: a) collecting a sample by capillary force to generate a collected sample in a first region of a device; b) separating the collected sample in a second region of the device or generating a first sample component and a second sample component from the sample in a second region of the device using a centrifugal force or forces (e.g., a first force to move the sample into the second region and a second force to separate components of the sample); and c) drawing the sample or first sample component by capillary force into a third region of the device to generate a metered and/or purified sample. In some embodiments, the method further comprises the step of: d) removing the sample or first sample component from the device using a centrifugal force. In some embodiments, the first region and/or third region comprise a porous membrane. In some embodiments, the centrifugal force is greater than the capillary force.

Further provided herein are methods comprising: processing a sample in a device comprising one or more wicking zones that transport liquid sample in multiple directions (e.g., any direction) and one or more spinning zones that transport liquid sample radially away from an axis of rotation.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the terms "subject" and "patient" refer to any animal, such as a dog, cat, bird, livestock, and particularly a mammal, preferably a human.

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, and industrial samples. Such examples are not however to be construed as limiting the sample types applicable to the present invention.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

DESCRIPTION OF THE DRAWINGS

These and other features, aspects, and advantages of the present technology will become better understood with regard to the following drawings.

DETAILED DESCRIPTION

To perform rapid, accurate and low-cost diagnostic tests at point of care, specimens should be collected without venipuncture and processed with minimal manual steps and equipment. The technology provided herein uses both capillary and centrifugal forces (centrifugal force is a "fictitious force" since it results from accelerating the device, not from physical interaction between two objects) in one device to collect and process specimens, achieving this goal.

The technology finds use in a wide variety of applications. For example, the devices, systems, and methods find uses where blood samples are collected from puncture sites in fingers or heels, or from primary collection vessels such as blood collection tubes, syringes or urine collection cups. For example, the devices, systems, and methods find use in any instance where a metered amount of a sample is desired and/or where a sample comprises two or more components (whether solid, liquid, or gas) and where there is a desire to at least partially isolate or purify one or more of the components. Biological samples, including but not limited to blood, blood components (e.g., plasma, serum), saliva, urine, cerebral spinal fluid, lacrimal fluid, bronchoalveolar lavage fluid, synovial fluid, nipple aspirate fluid, tear fluid, amniotic fluid, biofilms, wound components, cell culture, culture media, exosomes, proteins, nucleic acids, lipids, cell membranes or membrane components may be used.

Likewise, environmental samples including but not limited to surface matter, soil, mud, sludge, biofilms, water, or industrial samples may be used. Any two components of such a sample that are separable by centrifugal force may be isolated or purified (partially or entirely) using the devices, systems, and methods. Further, any amount of a pure sample or separated sample may be metered using the devices, systems, and methods.

The devices, systems, and methods find particular use for the metering and/or separation of plasma from blood to allow subsequent analysis of the plasma (e.g., for proteins, nucleic acid, metabolites, infectious disease components or markers, etc.). Such applications include, but are not limited to, collecting blood and dispensing plasma for testing at point of care; collecting blood and dispensing pre-treated plasma for transport to a remote laboratory; collecting blood, transfer plasma to a pad and dry for transport to a remote lab; and collecting blood and performing tests at point of care.

The systems, devices, and methods employ capillary and centrifugal forces to prepare samples and, in some embodiments, perform diagnostic, screening, or other analytical tests. Centrifugal forces are generated by spinning the device or a component of the device.

Capillary forces are generated with porous media such as glass fiber membranes. Centrifugal force dominates when the device is spinning. Capillary forces dominate otherwise.

By alternating centrifugal and capillary forces, sample metering and/or separation and isolation are facilitated. Any number of such steps may be employed, permitting complex processing of samples.

Centrifugal force moves fluids radially away from the axis of rotation out of capillary media and, as desired, separates components of heterologous samples that are amenable to separation by centrifugation (e.g., components having different densities (i.e., differing in specific gravity) such as separating cells from plasma from a blood sample). Capillary forces, when materials are positioned correctly, move fluids radially away from the axis of rotation (e.g., draw fluids into the device). Both forces run until equilibrium is obtained. The stable end points contribute to the precision of the device.

The devices may be configured in any way to accomplish the combination of alternating centrifugal and capillary forces. While simple devices may be preferred from a cost and ease of use standpoint, very complex devices involving a large number of alternating centrifugal and capillary forces may also be used, where desired. For example, in some embodiments, use of a device involves (cp=capillary; cf=centrifugal): cp sample collection; cf sample separation; and cp sample isolation. In other embodiments, the device involves cp sample collection; cf sample separation; cp sample isolation; and cf sample collection. In other embodiments, the devices involves cp sample collection; (cf sample separation; cp sample isolation)$_n$, where n=2 to or more (e.g., 2-5, 2-10, 2-20, 2-50, 2-100). In such embodiments, a variety of different or the same centrifugal and/or capillary forces are employed at each stage to differentially separate and isolate different components or to ensure full separation and isolation of components. For example a sample comprising components A, B, C, and D, each having different densities, may undergo a first separation/isolation combination that separates AB from CD and moves CD to a new zone. A second separation/isolation combination separates C from D and moves D to yet another new zone where it is ultimately collected and analyzed.

In some embodiments, where low cost, ease of use, and durability are desired, the device has no moving parts.

In some embodiments, the portions of the device that generate capillary forces employ membranes having pores. In most microfluidic devices, capillary forces are generated by the walls of the channels. In embodiments of the devices herein that employ porous membranes, capillary forces are generated by surfaces in the pores of the membranes (e.g., that are inserted into one or more channels of the device). This has the advantage of generating large capillary pressures without constraining the dimensions of the channels or requiring their surfaces to be hydrophilic, greatly simplifying manufacturing. While such embodiments may often be preferred, traditional capillary channels may be employed.

Any type of porous membrane able to provide the capillary forces and collect a sample may be employed. Such porous membranes include materials composed of nylon, nitrocellulose, mixed cellulose esters, polysulfones, and the like. A fibrous membrane, such as, for example, glass, polyester, cotton, or spun polyethylene may be used.

There are other advantages of using porous media to generate capillary pressure: some samples, such as blood samples containing plasma can be extracted from both the cell-depleted and cell-enriched phases since plasma flows much faster than cells in the membrane. This reduces the volume of sample required and makes the device more robust to variations in, for example, blood volume and hematocrit. Stop junctions are not required since flow stops when it reaches the end of the membrane. Reagents can be dried down in the membrane that are subsequently rehydrated and mixed with sample or sample components (e.g., plasma) as it flows in. By overcoming capillary forces with centrifugal forces, flow through the membranes can be controlled. This allows fluids to be stopped in membranes or to be completely eliminated from them.

In some embodiments, the device employs chambers that move fluids in three dimensions as opposed to two dimensions. This is accomplished, for example, by employing tiered chambers. Most microfluidic devices are 2D where fluids move only in a plane. The 3D geometry provided herein enables a tradeoff between depth and width and height of chambers, which allows the device to fit into small diameter tubes. For example, in some embodiments, it is possible to insert the device into a 5 mm diameter tube (e.g., for centrifugation). 3D fabrication also allows variable depths within a single tier. The depth of the collection chamber, which holds the collection pads, can be less than the separation chamber, which holds the sample after it is spun out of the collection pad. This allows the collection section to have a larger height-width area than the separation chamber. The larger area above makes collection more reproducible, while the smaller area below allows the bottom of the device to fit through a small orifice.

Sample collection can be by any desired mechanism. In some embodiments, a fluid sample (e.g., blood from a puncture site in a finger or heel; water from an environmental source) is directly contacted with a porous membrane in the sample collection zone. In other embodiments, a sample is collected by a collection instrument (e.g., tube (e.g., VACUTAINER blood collection tube), syringe, etc.) and then transferred to the sample collection zone. Direct contact has the advantage of not needing any additional materials or equipment for sample collection. This enables, for example, a single device to be used for collecting blood samples directly from heel or finger sticks, separating out cells, and aliquoting a specified volume of plasma.

After a component of the sample is isolated or purified by the device and collected, it may be analyzed by any desired technique. Such techniques include, but are not limited to, immunoassays (e.g., ELISA), mass spectroscopy, electrophoresis, photometry, electrochemistry, cytometry, refractometry, densitometry, turbidimetry, PCR, affinity binding, microarray analysis, sequencing, chromatography, or the like for detection of one or more of proteins, nucleic acids, carbohydrates, lipids, metabolites, ions, toxins, small molecules, or other molecules or properties of interest.

Provided below is an exemplary design optimized for separation and collection of plasma from a blood sample. This same design will find use with other sample types. It should be understood that variations on this configuration may be made to enhance performance for different sample types. Exemplary formulas are provided to assist with selecting dimensions, volumes, and other parameters based on the desired sample and result.

Device for Collecting Blood and Dispensing Plasma

An embodiment of the technology for collecting blood and isolating and dispensing plasma is described. This embodiment of the technology uses capillary and centrifugal forces to: collect a metered volume of blood; separate cells from plasma; aliquot a volume of plasma; and dispense the plasma into a detachable container.

Capillary and centrifugal forces accomplish these functions in the following steps: a) capillary action draws blood into a porous membrane; centrifugal force drains blood into a chamber and separates cells; capillary action draws plasma into a porous membrane; and centrifugal force discharges plasma into a detachable container.

While the device can be constructed from any desired material and most efficiently is constructed from an injection-molded core with heat-sealed front and back cover films, the prototype described in the experimental example section below was constructed using laser-cut sheets of plastic and transfer adhesive. The device comprises two tiers. A front or top tier and a back tier. FIG. 1 shows an exemplary embodiment with the front tier on the left and the back tier on the right. In assembled form, the bottom tier resides below the top tier. For centrifugation, the device is placed in a centrifugation tube (e.g., a 15 ml tube). When the device and tube are loaded onto a spinner disc, they are in the plane of the spinner, and consequently gravity is directed at right angles to the long axis. The top section 102 is closest to the axis of rotation of the spinner and the bottom is furthest. Centrifugal force is directed down the long axis of the device and tube, with an additional Coriolis component directed to the left as the device rotates counter clockwise to the right.

Referring to FIG. 1, the collect/separate tier 100 (left) contains a sample collection pad 110 and the separation chamber 120. The top section 102, is shaped like a nemes. The meter/discharge tier 200 (right) contains a plasma metering pad 210 and discharge channel 220. The two tiers are separated by a septum that has a slit opening 150 which connects the plasma pad to the separation chamber.

The core of the collect/separate tier, which forms the walls of the chambers, is a 1 mm thick sheet of PETG (Polyethylene Terephthlate Glycol-Modified) shim stock. The sample collection pads are located in the upper, circular chamber; and rectangular separation chamber is located immediately below it. There is a vent 130 above the sample pad that allows air in during the first spin. The front and back of the chambers are covered by 0.25 mm thick PET (Polyethylene Terephthlate) films, which are bonded to the core with 3M transfer adhesive (9472LE Adhesive Transfer Tape). The front cover has a circular opening slightly smaller in diameter than the collection pad. The opening is closed with a circular sticker after the pad is filled with blood. The septum forms the back of this tier. It has a slit opening 150 through which plasma and cells can pass.

The core of the meter/discharge tier is a 0.25 mm thick sheet of PET. The plasma-metering pad has an apple-shaped reservoir section 240 at the top with two branches extending out the bottom. The right branch 250 is the inlet that draws plasma by capillary action through the slit 150 in the septum and saturates the pad. The left branch 260 is the outlet that carries plasma to discharge channel under centrifugal force. The front of this tier is covered with the septum, and the back with a 0.25 mm thick sheet of PET that has a vent 270 above the reservoir.

Figure 2:
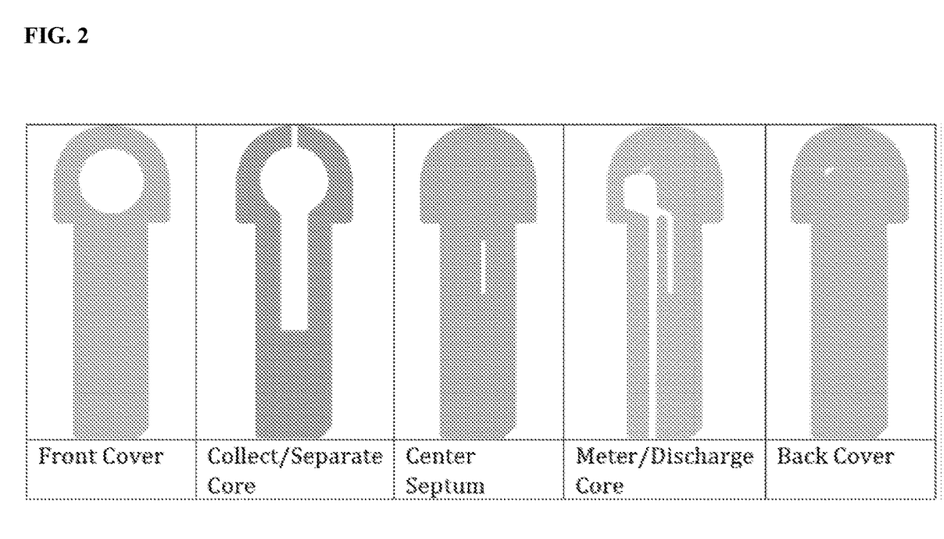
FIG. 2 shows a diagram of five layers (front cover, collect/separate core, center septum, meter/discharge core, and back cover) that may be used, in some embodiments, to assemble a device.

FIG. 2 shows five layers that may be used to assemble the two tier device, including front and back covers and a center septum. The five layers of the device are assembled in a fixture to keep them aligned. The collect/separate and meter/discharge cores are laser cut with 3M transfer adhesive on both sides. The parts are assembled in the following order: 1) attach septum to the collect/separate core, 2) insert sample pads into the circular chamber, 3) attach front cover to the collect/separate core, 4) attach meter/discharge core to the septum, 5) insert plasma pad into the meter/discharge core, and 6) attach back cover to the meter/discharge core.

Spinning is conducted via any desired mechanism. The experimental examples below employed a modified Eppendorf 5702 centrifuge with a swing-bucket. Two of the buckets were locked into horizontal positions by inserting a threaded nylon rod into opposing wells. Two nuts on the rod were tightened against the tops of the buckets to lock them into place. Two 15 ml Falcon tubes were cut off so their tops were 4.5 mm above the tops of the horizontal carriers. Devices were placed in one of Falcon tubes and the other was filled with Kimwipe tissue to balance the rotor.

The top of the tube, against which the bottom of the nemes rested, was determined to be 37 mm from the axis of rotation. All centrifugal force and pressure calculations were made using this reference point and the rpm setting on the display. As an example, if the bottom of the separation chamber is 24 mm below the reference line, it would be 61 mm from the axis of rotation. At the maximum rpm setting of $4.4 \times 10^3$ rpm, the angular speed of rotation, $\omega$, would be 461 rad/s. The centrifugal acceleration, which is given by:

$$F = \omega^2 \cdot r$$

would be 12,951 m/s, where r is converted from millimeters to meters. The relative centrifugal force (RCF), which is the ratio of F to g, the acceleration due to gravity on the surface of earth, would be 1,321.

In order to have separation efficiencies greater than 95%, it is preferable to have an RCF of 10× this amount, which is achieved by increasing the rpm by a factor of the square root of 10=3.16. For such embodiments, a different centrifuge and use of more robust materials for the transfer adhesive should be used.

The step-by-step operation of the device is described in the following FIG. 5-8, each of which shows the interiors of both tiers. The discharge tube is only shown in the last step. The collect/separate tier, on the left, contains the sample collection pad, the separation chamber, and the opening through the septum. The meter/discharge tier, on the right, contains the plasma metering pad and the discharge channel.

In some embodiments, the collection/separation/metering device and discharge tube are not attached for the blood collection step. This enables the discharge tube to be pre-filled with a liquid buffer and stored in a vapor-tight package.

The main features of the collect/separate tier are: vent to allow air into the top of sample pad during spinning; sample pad sized to absorb specified volume of blood; separation chamber to hold blood released from the sample pad; and the slot through the septum where blood enters the inlet branch of the plasma pad. The main features of the meter/discharge layer are: vent through back cover to allow air to enter the reservoir of the plasma pad; shorter inlet branch which transports blood from the separation chamber to the reservoir; longer outlet branch.

Figure 3:
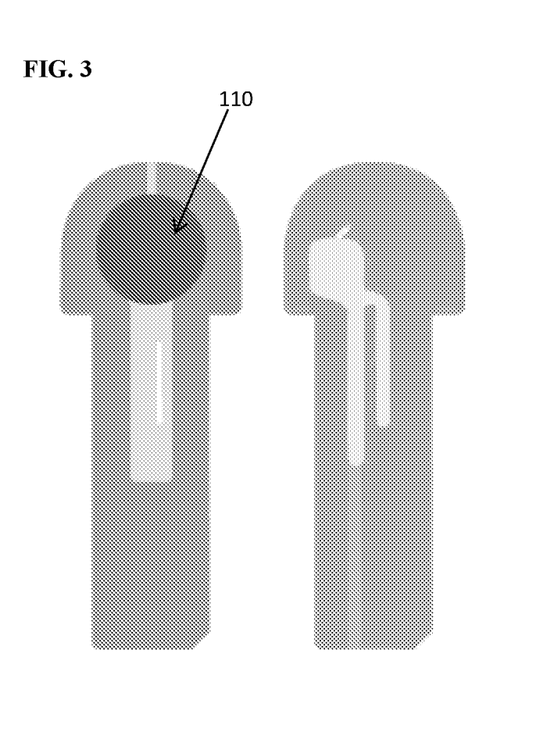
FIG. 3 shows a diagram of an embodiment of a device showing a first step in a sample processing process with sample added to a sample collection zone.

In this front-fill configuration, drops of blood (e.g., from a heel or finger stick) are drawn into the collection pad 110 by capillary action. The pad and chamber are sized to hold a specified volume of blood. When the pad is completely red (shown as a darker color pad in FIG. 3, then the required volume has been collected.

Figure 4:
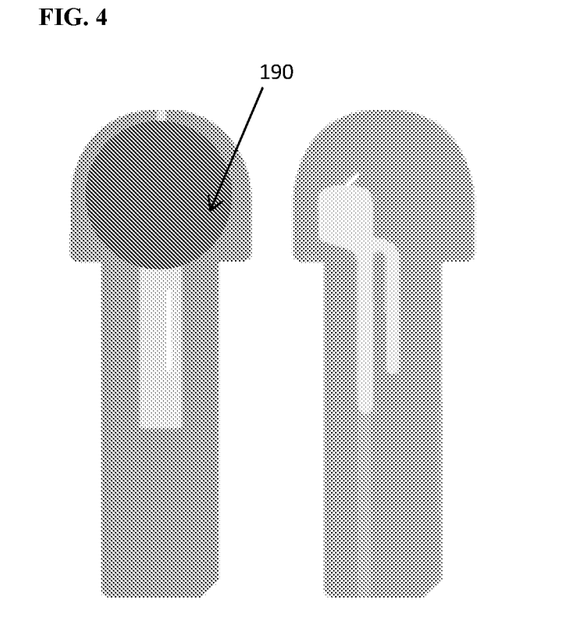
FIG. 4 shows a diagram of an embodiment of a device showing a second step in a sample processing process with a cover placed over the sample collection zone to prevent evaporation.

As shown in FIG. 4, an adhesive sticker 190 is placed over the opening in the front cover to prevent evaporation during spinning. The evaporation loss can be as large as 10 to 15 μl when the pad is exposed to the air stream in the spinner. An alternative configuration that fills from the top end instead of the front may be used to eliminate the need for a separate cover (see e.g., FIGS. 9 and 10).

The device is joined to the discharge tube and they are placed in the spinner. They are oriented horizontally with the long axis normal to the axis of rotation so gravity does not act when spinning stops. Otherwise, there may be some siphoning of plasma from the inlet to the outlet of the plasma metering pad.

Figure 5:
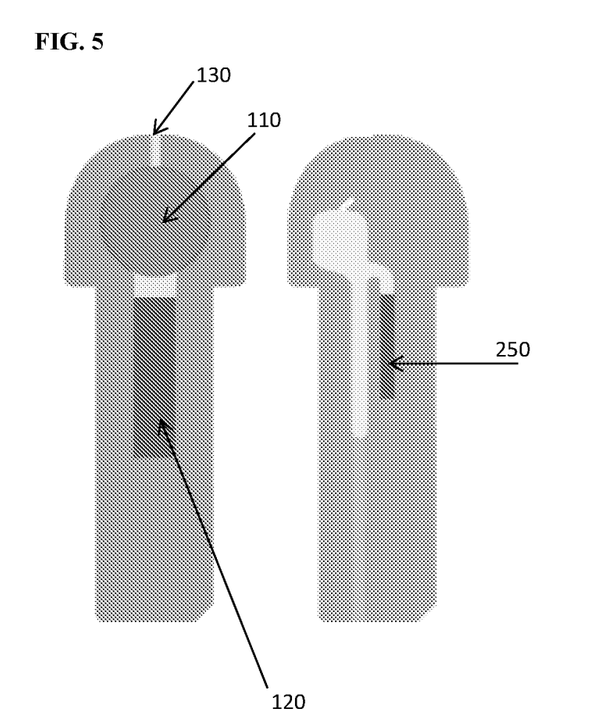
FIG. 5 shows a diagram of an embodiment of a device showing a third step in a sample processing process with the sample moved by centrifugal force to a reservoir.

As shown in FIG. 5, when spinning begins, blood is drained from the plasma collection pad 110 into the separation chamber 120 as soon as centrifugal pressure become greater than capillary pressure (the darker color in chamber 120 representing blood pulled into the chamber). The centrifugal pressure can be estimated from the following formula:

$$Pspin = \frac{1}{2} \cdot p \cdot \omega^2 \cdot (r_2^2 - r_1^2)$$

where $\rho$ is the density of plasma, $\omega$ the angular speed of rotation, r1 and r2 the distances, respectively, of top and bottom of the sample pad from the axis of rotation.

As blood drains from the pad, it is replaced by air that enters through the vent 130 in the top of the device. Air in the separation chamber, which is displaced by blood, escapes through the metering pad inlet and the vent above the reservoir section.

Most of the blood spun out of the sample pad is contained in the separation chamber 120, however a few microliters may enter the inlet branch 250 of the metering pad. It will flow up to slightly above the level of blood in separation chamber. The distance between the level of blood in the inlet and the level in the separation chamber is determined by the difference in the capillary and centrifugal pressures. The dimensions of the separation chamber, length of the inlet and speed of rotation are preferably designed and selected so blood that will not reach the reservoir section of the metering pad during the separation spin, which prevents siphoning into the outlet section.

The depth and width of the separation chamber are set so that the height of blood ejected from the collection pad will be below the point where the inlet and outlet branch off from the reservoir section of the metering pad. The length of the inlet section is sufficiently long to reach the cell-plasma interface for the worse case combination of low blood volume and high hematocrit. The speed of rotation should be as fast as possible to get the most efficient separation.

Figure 6:
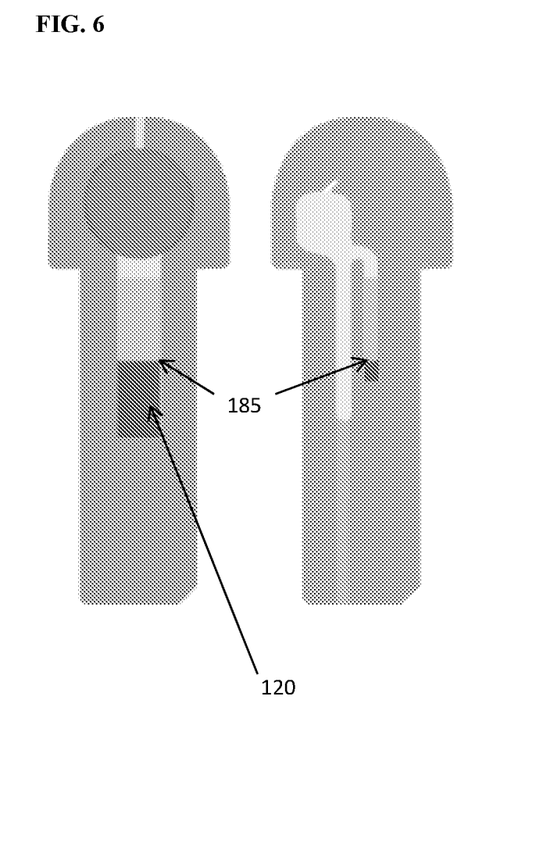
FIG. 6 shows a diagram of an embodiment of a device showing a fourth step in a sample processing process with the sample separated into two components in the reservoir.

As shown in FIG. 6, after a few minutes spinning, the cells sediment toward the bottom of the separation chamber and an interface 185 forms between the cell-depleted and cell-rich phases. The spinning also clears cells from most of the inlet branch of the metering pad and only a few remain trapped in the pores and sedimented at the bottom. The blood that enters the plasma pad during the spin probably rises less than 1 mm above the level of blood in the separation chamber because centrifugal pressure is very much greater than capillary pressure.

Figure 7:
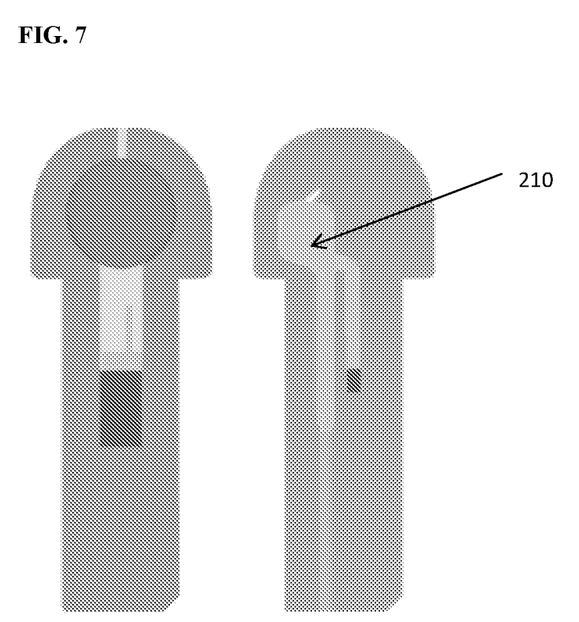
FIG. 7 shows a diagram of an embodiment of a device showing a fifth step in a sample processing process with an isolated component of the sample transferred to the sample metering zone of the second layer.

As shown in FIG. 7, when separation is sufficiently complete so there is an adequate volume of plasma above the interface, spinning is stopped. Capillary pressure is then dominant in the metering pad 210 and it fills to saturation with plasma. The rate of filling can be predicted by the Washburn equation:

$$L_{lf} = \sqrt{\frac{\gamma D_e \cos(\theta)}{4\mu} t}$$

where $L_{lf}$ is the location of the liquid front in the porous medium, t the time, $\gamma$ the liquid surface tension, $\mu$ liquid viscosity, $\theta$ the contact angle between the liquid and the porous media, and $D_e$ the effective pore diameter.

The reservoir is placed just above the inlet to minimize the distance plasma flows to saturate the pad. The longest flow path is to the end of the outlet, which should be below the inlet to drive plasma in that direction during the discharge spin. The geometry of the inlet-reservoir-outlet junction is designed to direct discharge down the outlet branch.

Figure 8:
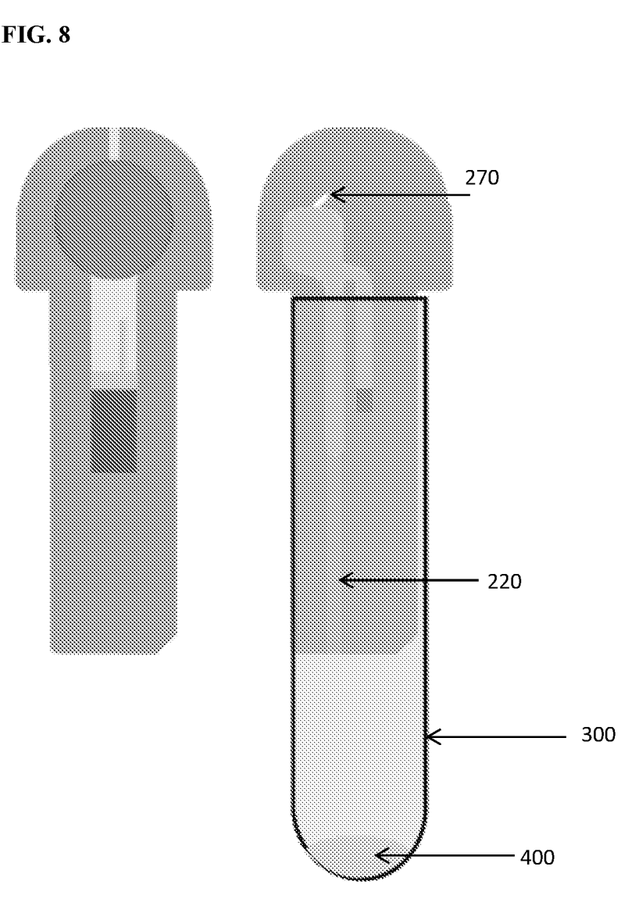
FIG. 8 shows a diagram of an embodiment of a device showing a sixth step in a sample processing process with sample removed from the device into a collection tube by centrifugal force.

As shown in FIG. 8, in a second, discharge spin, the reservoir and outlet sections of plasma-metering pad are drained through the discharge channel 220 into the attached tube 300, with isolated plasma 400 collected in the bottom of the tube. The contents of the inlet are drained back into the separation chamber. Plasma in the pad is replaced by air that enters through the vent 270 above the reservoir (the stem on the apple). When the discharge spin stops, the metering pad refills with excess plasma and RBCs (not shown).

To dispense a given volume of plasma, the volume of whole blood required depends primarily on the separation efficiency of the spinner and the maximum hematocrit which will be encountered. In addition, the separation efficiency depends on the relative centrifugal force applied, which depends on distance of the separation chamber from the axis of rotation, the speed of rotation, and the duration.

For a separation efficiency, s, and a hematocrit, h, the volume of plasma, p, available from a volume of blood, b, is given by:

$$p = \frac{1-h}{s} \times b$$

If the separation efficiency is 0.80 and the hematocrit is 0.55, 100 µl of blood will produce at most 31 µl of plasma with no red blood cells.

The void volume of the metering pad's reservoir and outlet should equal the target plasma dispense volume. Plasma and cells in the inlet are returned to the separation chamber during the second (discharge) spin.

The void volume of Ahlstrom 8964 absorption fibers is approximately 97% of the material volume.

Figure 9:
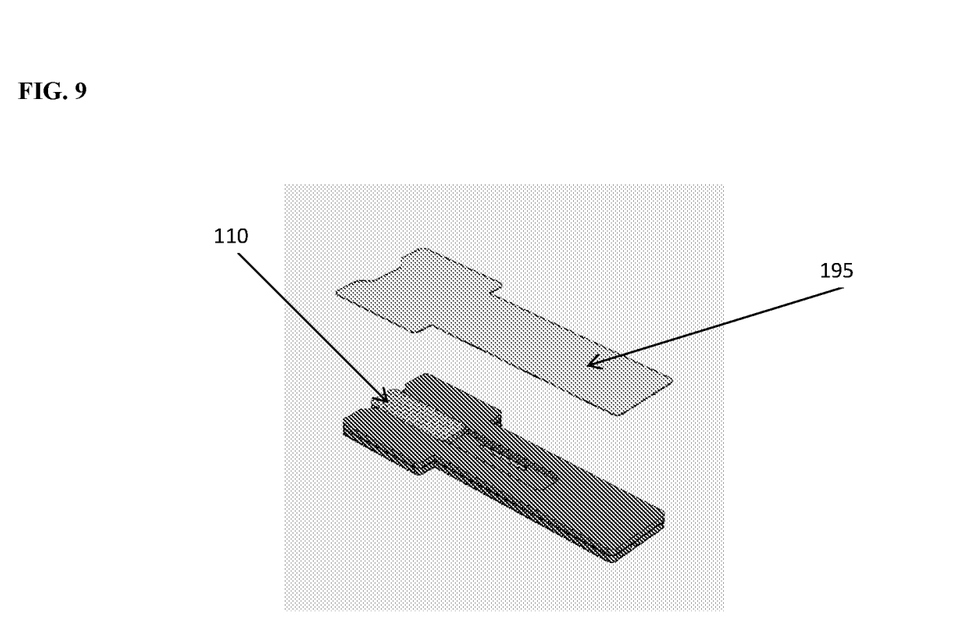
FIG. 9 shows a diagram of an embodiment of a device showing a end loaded device in three-dimensional rendering with a top cover shown above the device with the sample collection zone and separation zone shown on top.
Figure 10:
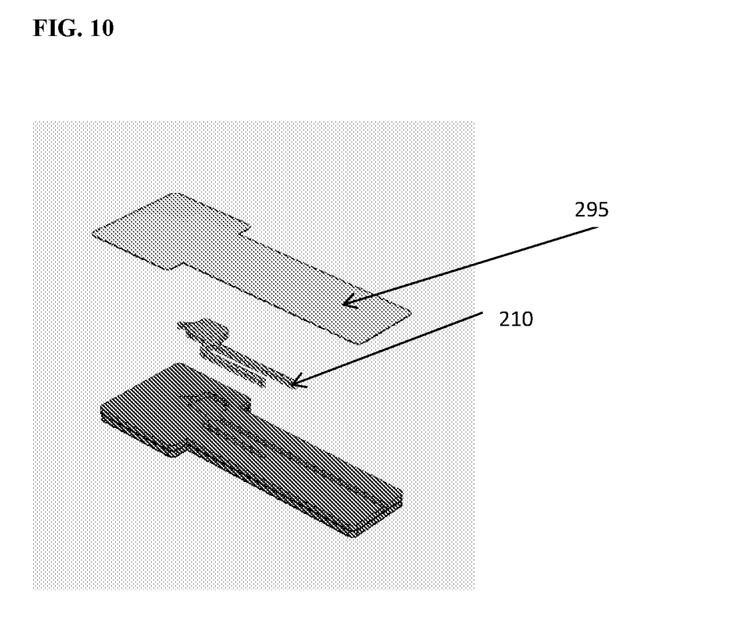
FIG. 10 shows a diagram of the opposite side of the device shown in FIG. 9, showing an end loaded device in three-dimensional rendering with a bottom cover shown above the device with the sample metering zone shown on top.

FIGS. 9 and 10 show a top-loaded or end-loaded embodiment of the device. The device is prepared as a single mold. FIG. 9 shows one side of the mold with the sample collection zone and separation zone on top and showing an inserted porous membrane 110 oriented to be exposed at the top of the device. A film 195 is shown, which is adhered to the device to seal the sample collection zone and separation zone. When sealed, the top of the porous membrane 110 is exposed on the outside of the device and able to bring contacted sample into the device by capillary force. FIG. 10 shows the other side of the mold with the sample metering zone on top. A porous membrane 210 is shown sized to fit within the sample metering zone. A second film 295 is shown, which seals the sample metering zone when applied after the porous membrane is added.

Data collecting using such a device is provided in the experimental section below. Several highly beneficial innovative features were observed. Placing the reservoir above the separation chamber was a significant development. It minimized the distance plasma would have to flow, and thus shortened the wait between spins. Locating the inlet and outlet at the bottom of the reservoir contributes to the accuracy and precision of the discharge volume. During the second, discharge spin, plasma in the reservoir and outlet flows into the discharge channel while plasma and cells in the inlet flow back into the separation chamber. Almost all of the plasma above the red blood cell (RBC) interface can be discharged, since RBCs in the inlet will be returned to the separation chamber on the second spin. The porous membrane transports plasma preferentially over cells, which enables the opening between the separation chamber and the metering membrane to extend into the red cell phase. This makes the device much more tolerant to variations in sample volume and hematocrit.

Examples

Capillary Pressure

Capillary pressure generated by the Ahlstrom 8964 material was estimated by both the capillary rise and air entry methods. The capillary rise method determines the distance that the liquid front travels up a strip of membrane. A 5 mm wide strip was inserted into a bottle of colored water and the front rose 59 mm above the liquid. It was repeated with both sides of the membrane covered with Parafilm to prevent evaporation, and the front rose 54 mm.

Capillary pressure was calculated to be 529-578 N/m$^2$ from the formula $$Pcap = \rho \cdot g \cdot h$$

where $\rho$ is the density of water, g the standard acceleration of gravity, and h the height of the liquid front.

The air entry method of estimating capillary pressure finds the rpm at which air begins to replace liquid in a saturated membrane. A rectangular strip of Ahlstrom 8964 was inserted into the device saturated with colored water. It was placed in the centrifuge and the rpm were increased from 100 in increments of 100. The liquid discharged was captured in a chamber below the wick and its volume estimated after each spin by measuring the height.

At 300 rpm (3.4 RCF) no liquid had been discharged. At 400 rpm (6.0 RCF), the first drops appeared in the discharge chamber, implying air had begun to enter the membrane. Using the formula $$Pspin = \frac{1}{2} \cdot p \cdot \omega^2 \cdot (r_2^2 - r_1^2)$$

the capillary pressure was estimated to be 483-858 N/m2, which is consistent with the capillary rise results.

More accurate estimates can be obtained if desired by measuring the bubble point, but the centrifugal forces needed to get rapid, efficient separation of cells and plasma are generally orders of magnitude greater than the capillary pressure.

Separation Efficiency

Separation efficiency, which is the ratio of observed interface location to one predicted by the hematocrit, was estimated for the device where the bottom of the separation chamber was 64 mm from the axis of rotation. When spun at 3600 rpm, the RCF was 929 xg and the separation efficiency after 5 minutes was 81%.

Plasma and Red Cell Flow Through Membrane

To confirm that red cells will flow through the porous media, but lag behind plasma, a strip of Ahlstom 8964 was inserted into a tube of blood which had been separated. This feature is needed to extract all of the available plasma from blood for high hematocrit or low volume samples. If red cells can flow up the inlet, then it will not be necessary to have surplus plasma to drain back into the separation chamber.

Effect of Inlet and Outlet Lengths

To determine if a longer outlet would siphon liquid from the inlet, two metering pads were fabricated with outlet branches of different lengths. Both had inlets approximately 13 mm long (void volume of approximately 6.8 µl), while one had an outlet 18 mm long and the other 23 mm long. The volume of liquid returned to the separation chamber was measured by the height of the meniscus.

The pads were saturated with colored water added directly to the top of the reservoir through the air vent. 40 µl was required to saturate the pad with the shorter outlet, 45 µl for the longer-outlet pad. The difference in volumes was approximately the difference in the volumes of the outlet membranes.

The volume returned in both cases was close to the void volume of the inlet, 7.3 and 6.7 µl, indicating the liquid was not siphoning from the inlet to the outlet.

Collection Volume

The volume of blood required to saturate the sample collection pad was estimated by drawing anti-coagulated blood from a capillary tube. Aliquots of approximately 20 µl were transferred to the collection pad until it was completely red. The mean volume collected for 3 replicates was 128.3 µl with a standard deviation of 2.2 µl and CV of 1.7%

Repeatability

The repeatability of the discharge volume was determined for 3 replicates of 120 µl samples of an EDTA blood specimen with 45% hematocrit. The mean volume discharged was 37.8 µl with a standard deviation of 1.5 µl.

Evaporation Effects

To determine if liquid in the collection pad and/or discharge tube was being lost to evaporation, the weight of the device before the first spin was compared to the sum of the device weight after the second spin plus the weight gain by the discharge tube. It was found that approximately 10 µl was lost during spinning.

When the sample pad opening was covered with an Avery sticker, the volume lost was reduced to approximately 5 µl. Further experiments showed that approximately 2-3 µl was still lost during the first spin to evaporation from the sample pad through the small air vent in the Avery sticker.

For all subsequent studies, the volume of plasma discharged was estimated from the weight lost by the device between the first and second spins. Since the sample pad was drained in the first spin, it could be assumed that the evaporative losses would be small during the second spin.

For this configuration, the amount of weight lost by the device between the first and second spins would be more accurate than the weight gained by the discharge tube.

Evaporative losses for an end-fill configuration (see e.g., FIGS. 9 and 10), which had no sticker covering the exposed section of the pad, were 2-3 µl during the first spin. These could be reduced by covering the back side with the septum film.

Hematocrit Effects

The effect of hematocrit on the discharge volume was determined for five contrived samples between 35 and 55%. The discharge volume, ranged between 32.4 and 35.9 across all hematocrits.

Blood Volume Effects

The effect of the volume of blood collected on the discharge volume was determined by adding volumes above and below the target volume of 120 µl to devices. Volumes were pipetted onto devices for the design target (120 µl and 5% (114 µl) and 10% (108 µl) below the target µl. Additional samples were run that simulated collection from a heelstick. Blood was drawn from a capillary tube until the pad was completely red, which resulted in volumes greater than the target. The measured discharge volumes were all within 10% of the mean.

We claim:

1. A device for collecting and/or processing a sample, comprising:
   a) a sample collection zone comprising a porous membrane;
   b) a separation zone in fluid communication with said sample collection zone and positioned relative to said sample collection zone such that a centrifugal force applied along an axis of said device moves a collected sample from said sample collection zone to said separation zone;
   c) a sample metering zone comprising (i) an inlet branch, (ii) a reservoir, (iii) an outlet branch, and (iv) a porous membrane within the inlet branch, the outlet branch, and the reservoir; the inlet branch of said sample metering zone in passive fluid communication with a portion of said separation zone, but not said sample collection zone; wherein fluid that passes from the separation zone into the inlet branch will further passively pass into the reservoir and the outlet branch; wherein the reservoir and the outlet branch are configured to accept a defined volume of fluid; and
   d) a discharge channel in fluid communication with the outlet branch of said sample metering zone and positioned along said axis such that a centrifugal force applied along said axis moves an aliquot of said sample from the reservoir and the outlet branch of said sample metering zone to said discharge channel, but the geometry of the sample metering zone prevents fluid in the inlet branch of said sample metering zone from flowing to said discharge channel under the centrifugal force.

2. The device of claim 1, further comprising an air vent in fluid communication with said sample collection zone.

3. The device of claim 1, further comprising an air vent in fluid communication with said sample metering zone.

4. The device of claim 1, wherein said device comprises a slit opening between said separation zone and said sample metering zone.

5. The device of claim 1, wherein said device is fabricated or molded as a single part having a first side comprising said sample collection zone and said separation zone and a second side comprising said sample metering zone.

6. The device of claim 1, wherein said device comprises two layers: a) a first layer comprising said sample collection zone and said separation zone; and b) a second layer below said first layer, said second layer comprising said sample metering zone.

7. The device of claim 6, further comprising a third layer disposed between said first layer and said second layer, said third layer comprising a slit opening between said separation zone and said sample metering zone.

8. The device of claim 6, further comprising a first cover configured to cover said sample collection zone.

9. The device of claim 8, further comprising a second cover configured to cover said sample metering zone, said second cover comprising an air vent in fluid communication with said sample metering zone.

10. The device of claim 1, wherein said porous membrane comprises an anti-coagulant, stabilizing reagent, or assay reagent.

11. A kit comprising a device of claim 1 and a collection tube.

12. A method comprising metering a sample or isolating a component of a sample using a device of claim 1, wherein said method comprises: a) contacting said porous membrane in said sample collection zone with said sample such that said sample enters said porous membrane via capillary forces; b) applying centrifugal force to said device along said axis to move at least a portion of said sample from said sample collection zone to said separation zone and, optionally, to separate said sample into a first component and a second component; c) reducing or stopping said centrifugal force such that said sample or first component in said separation zone moves via capillary force into said sample metering zone; d) applying centrifugal force to said device along said axis to move a portion of said sample or first component located in said reservoir and outlet branch out of said device through said discharge channel; and e) capturing said sample, or first component in a vessel.

13. The method of claim 12, wherein said sample is a blood sample and said first sample component is plasma.

* * * * *